United States Patent [19]

Kelman et al.

[11] Patent Number: 5,476,515
[45] Date of Patent: Dec. 19, 1995

[54] METHOD OF MAKING INTRAOCULAR LENSES WITH INJECTABLE COLLAGEN-BASED COMPOSITIONS

[75] Inventors: Charles D. Kelman, New York, N.Y.; Dale P. DeVore, Chelmsford, Mass.

[73] Assignee: Autogenesis Technologies, Inc., Acton, Mass.

[21] Appl. No.: 158,019

[22] Filed: Nov. 24, 1993

Related U.S. Application Data

[63] Continuation of Ser. No. 740,838, Aug. 6, 1991, abandoned.
[51] Int. Cl.$^6$ .................................................. A61F 2/16
[52] U.S. Cl. .................. 623/6; 623/4; 623/901; 606/107; 424/424; 424/427
[58] Field of Search ................................. 606/107; 623/4, 623/6, 901; 424/424, 427

[56] References Cited

U.S. PATENT DOCUMENTS

| | | |
|---|---|---|
| 3,121,049 | 2/1964 | Nishihara . |
| 3,131,130 | 4/1964 | Oneson . |
| 3,314,861 | 4/1977 | Fujii . |
| 3,553,299 | 1/1971 | Thiele et al. .................... 623/4 |
| 3,949,073 | 4/1976 | Daniels et al. .................... 424/177 |
| 4,002,169 | 1/1977 | Cupler, II .................... 606/107 |
| 4,126,904 | 11/1978 | Shepard . |
| 4,223,984 | 9/1980 | Miyata et al. .................... 351/160 |
| 4,233,360 | 11/1980 | Luck et al. .................... 428/210 |
| 4,242,291 | 12/1980 | Hughes et al. .................... 351/160 H |
| 4,268,131 | 5/1981 | Miyata et al. .................... 351/160 |
| 4,388,428 | 6/1983 | Kuzma et al. .................... 523/106 |
| 4,427,808 | 1/1984 | Stol et al. .................... 524/24 |
| 4,488,911 | 12/1984 | Luck et al. .................... 106/161 |
| 4,581,030 | 4/1986 | Bruns et al. .................... 623/5 |
| 4,608,050 | 8/1986 | Wright et al. .................... 623/4 |
| 4,713,446 | 12/1987 | DeVore et al. .................... 530/356 |
| 4,748,152 | 5/1988 | Miyata et al. .................... 514/2 |
| 4,851,513 | 7/1989 | Devore et al. .................... 530/356 |
| 4,969,912 | 11/1990 | Kelman et al. .................... 623/66 |
| 4,983,181 | 1/1991 | Civerchia .................... 623/5 |
| 4,994,081 | 2/1991 | Civerchia et al. .................... 623/5 |
| 5,002,571 | 4/1991 | O'Donnell, Jr . et al. .................... 623/6 |
| 5,294,314 | 3/1994 | Nesburn et al. .................... 623/6 |
| 5,354,336 | 10/1994 | Kelman et al. .................... 623/6 |

OTHER PUBLICATIONS

Guyton, R. C. "Medical Physiology", 6th edition, W. B. Saunders Co.; Philadelphia, Pa., USA; 1981; pp. 724–635.
Toats, F. M. (1972) *Physiol. Rev.* vol. 52, No. 4, pp. 828–858.
Witkovsky, P. (1971), *Annu. Rev. Physiol.* vol. 33, pp. 257–273.
"Merck Manual" 15th Edition, R. Berkow and A. J. Fletcher, editors; Merck, Sharpe and Dohme publishers, 1987, pp. 2207–2211.
"Merck Manual" 15th Edition, Merck, Sharpe and Dohme publishers, 1987, p. 2227.
R. Van Heynengen, (1975) *Sci. Am.* vol. 233 (6) pp. 70–81.
S. A. Arshinoff (1986) *Curr. Can. Ophthalmic Pract.* vol. 4 (2), p. 64.
Apple, D. J., Geiser, S. C. and Isenberg, R. A. "Evolution of Intraocular Lenses," Univ. of Utah Printing Service, 1985.
D. P. DeVore (1991) *J. Long–Term Effects of Ophthalmic Medical Implants*, vol. 2 (manuscript, 25 pages).
M. E. Nimni in "Collagen: vol. I Biochemistry", CRC Press, Inc., Boca Raton, Fla. USA (1988), pp. 7–16.
F. H. Silver in "Biological Materials: Structure, Mechanical Properties, and Modeling of Soft Tissues", New York University Press; 1987, p. 143.
L. Civerchia–Perez, et al. (1980), *Proc. Natl. Acad. Sci. USA*, vol. 77, No. 4, pp. 2064–2068.
J. F. Woessner in "The Methodology of Connective Tissue Research," D. A. Hall, edition; Joynson–Bruvvers Ltd., Oxford; 1976, pp. 227–233.
E. Cotlier in "Adler's Physiology of the Eye: Clinical Application", 8th edition, R. A. Moses and W. M. Hart, editors; C. V. Mosby Co.; St. Louis, Mo. USA (1987), pp. 268–272.
G. Schramm, (1981), "Introduction to Practical Viscometry", pp. 1–8, Haake Viscommeters.
D. P. DeVore, et al., (1989) *Mat. Res. Symp.* vol. 110, pp. 455–461.
D. A. Gibbs, et al. (1968) *Biopolymers*, vol. 6, pp. 777–791.
L. M. Fisher, N.Y. Times, Jan. 29, 1991, Business Section

*Primary Examiner*—Paul B. Prebilic
*Attorney, Agent, or Firm*—Darby & Darby

[57] ABSTRACT

Injectable collagen-based compositions can be used in methods to fill a lens capsular sac, following lens extraction procedures, to form a new intraocular lens. Purified soluble or partially fibrillar collagen may be modified with acylating agents, sulfonating agents or combinations thereof to form a clear, transparent collagen composition having indices of refraction between about 1.2 to 1.6. The modified collagen may injected into a lens capsular sac to form an intraocular lens (IOL) in situ. The IOL is clear, transparent, resistant to epithelialization and is capable of accommodation. The collagen-based IOL produced by the method of the present invention may remain in its original viscous liquid state or may be polymerized into a soft gel. The collagen-based IOL may be used to replace diseased or natural lens to treat cataracts, presbyopia, myopia and hyperopia.

17 Claims, 3 Drawing Sheets

METHOD OF MAKING INTRAOCULAR LENSES WITH INJECTABLE COLLAGEN-BASED COMPOSITIONS

This application is a continuation of application Ser. No. 07/740,838, filed Aug. 6, 1991 now abandoned.

FIELD AND BACKGROUND OF THE INVENTION

As the primary organ of vision in vertebrate animals, the eye often compared to the usual photographic camera. In simplified terms, the eye has a lens system, a variable aperture system (the pupil) and a light-sensitive retina that corresponds to the film. The focusing ability of the eye resides within the crystalline lens which comprises a strong elastic capsule filled with viscous, transparent fibers of crystalline and albuminoid proteins. Far more complex and fragile than that of a mere camera lens, the crystalline lens of the eye is especially prone to damage due to disease, environmental factors and the aging process. For a review on the lens system, see, for example, Cotlier, E. in "Adler's Physiology of the Eye: Clinical Application", 8th edition, R. A. Moses and W. M. Hart, editors; C. V. Mosby Co.; St. Louis, Mo., USA (1987), pages 268–272.

The unique ability of the lens to change its shape or curvature to automatically adjust the focus of the eye for objects at different distances is known as accommodation. Accommodation occurs by muscular contraction and relaxation causing the elastic-like lens to change shape and increase its optical or refractive power. For a general discussion of the mechanism of accommodation, see Guyton, R. C. "Medical Physiology", 6th edition, W. B. Saunders Co.; Philadelphia, Pa., USA; 1981; page 724–735; Toats, F. M. *Physiol. Rev.* 52: 828, 1972; and Witkovsky, P., *Annu. Rev. Physiol.* 33: 257, 1971.

Accommodation is lost during the aging process primarily due to a hardening of the natural lens. Loss of accommodation due to a progressive denaturation of the lens proteins produces an abnormal condition commonly known as "presbyopia". Presbyopia generally affects individuals in the early to mid forties and the resultant gradual loss of visual acuity is generally treated with bifocal spectacles. For general discussion of presbyopia, see "Merck Manual" 15th Edition, Merck, Sharpe and Dohme publishers, 1987, page 2211 and Guyton, R. "Medical Physiology", 6th edition, W. B. Saunders Co.; Philadelphia, Pa., USA; 1981; page 724–735.

Lenticular cataracts are an especially common eye abnormality characterized by a progressive loss of vision beginning in middle age or later. In the early stage of cataract formation, the transparent protein fibers of the lens become denatured, presumably by oxidative damage due to the normal aging process. The denatured proteins then coagulate, forming the characteristic opaque areas in place of the normal transparent protein fibers of the lens. In the advanced stage, calcium deposition occurs on the coagulated proteins, thus further increasing the opacity. Cataract formation can also be accelerated by exposure to X-rays, heat from infrared rays, systemic disease (e.g. diabetes), uveitis, or systemic medications (e.g. corticosteroids). The degree of vision loss due to cataract formation can be ascertained by ophthalmoscopic slit-lamp examination which provides more details about the character, location, and extent the opacities. For a detailed discussion of cataract formation, see Van Heynengen, R. *Sci. Am.* 233(6): 70, 1975 and "Merck Manual", 15th Edition, Merck, Sharp and Dohme publisher, 1987, page 2227.

Frequent refraction corrections help maintain useful vision during cataract development. When a cataract has obscured light transmission so greatly that useful vision is lost, surgical intervention is necessary to extract the lens. Lens extraction can be accomplished by total removal of the lens, or by phacoemulsification of the lens followed by irrigation and aspiration, leaving the lens capsular sac intact. When this is done, however, the eye loses a large portion of its refractive power. Post-operative refractive correction to alleviate the visual defect is accomplished by cataract spectacles, contact lens, or intraoperative implantation of an intraocular lens.

Traditionally, cataract spectacles have produced less than satisfactory results because of induced visual distortions such as aberrant depth perception. For example, cataract spectacles with thick lenses are known to induce a Galilean telescopic effect which results in abnormally magnified images. Moreover, unilateral surgical removal of lenses makes correction of stereovision by such spectacles virtually impossible.

Contact lenses eliminates many of the aforementioned problems, however, the magnification problem remains. Furthermore, many patients are unable to tolerate contact lenses because of poor manual dexterity, insufficient tear production or lens hygiene problems.

Implantation of endocapsular lens or (as more commonly known) intraocular lens (IOL), on the other hand, has been widely accepted as the treatment of choice for correcting visual impairments following removal of diseased lenses. The remarkable success of IOL implantation is due to significant improvements in surgical instrumentation and technique as well as in the design and construction materials of IOLs.

Microsurgical procedures have been developed to remove cataract lenses through very small incisions in the capsular sac (see, for example, Arshinoff, S. A. *Curr. Can. Ophthalmic Pract.* 4(2):64, 1986 and Welsh, R. C. et al. *Cataract Surg NOW* 1(2): 21–22, 1983 for a discussion of capsulotomy surgical techniques). An IOL is then gently inserted into the intact capsular sac, positioned in place, and the wound is then closed with fine sutures. Conventional IOLs are generally fitted with surgical loops to fix and/or maintain the IOL in position. Materials which are used to fabricate the IOLs are typically rigid or semi-rigid plastics such as polymethyl methacrylate. Newer and softer fabrication materials include biocompatible hydrogels and silicones. For a general discussion of IOL development, see for example, Apple, D. J., Geiser, S. C. and Isenberg, R. A. "Evolution of Intraocular lenses," University of Utah Printing Service, 1985).

Conventional IOLs, however, have a number of deficiencies associated with their use. For a review of the complications of conventional IOLs, see for example, Apple, D. J. et al., (1984) *Ophthalmology*, Vol. 29, No. 1; Drews, R. C. (1982). *Trans. Ophthal. Soc. U.K.*, Vol. 102, page 498; DeVore, D. P. (1991) *J. Long-Term Effects of Medical Implants*, Vol. 2, in press. For example, implantation of conventional IOLs are known to induce excessive accumulation of epithelial cells lining the lens capsule. This interface of cells, in turn, results in opacification of the lens as well as a variety of pathological conditions which include pupillary occlusions, iris atrophy and secondary glaucoma. Moreover, Mechanical dislocation of the IOL frequently results in damage to the corneal endothelium. Another notable drawback is that none of the IOLs of the prior art have accommodative capacity.

With the capsular bag intact, a safe, effective injectable material that could be used to refill the capsular bag and which simulates the natural lens would be desirable. This material should have an index of refraction similar to that of the natural lens, but variable so that any refractive errors might be corrected. Such injectable lens would still be able to accommodate and therefore provide a dramatic advantage over current intraocular lens implants.

SUMMARY OF THE INVENTION

The present invention relates to a method of making an intraocular lens using injectable collagen-based compositions. Chemically modified collagen compositions with varying indices of refraction can be used in filling the intact lens capsular bag following removal of the damaged lens. The new prosthetic lens, having predetermined index of refraction, are capable of accommodation. The intraocular lens prepared by the method of the present invention can be used to replace natural or diseased lenses for treatment of cataracts, presbyopia, myopia and hyperopia.

The modified collagen compositions of the invention comprise viscous yet injectable solutions of purified, collagen modified with glutaric anhydride or other acylating agent or a sulfonating agent or a combination of the foregoing. The modified collagen solutions can be prepared with a specific index of refraction to provide optimum visual acuity. The choice of chemical modifier(s) and the extent of modification will ultimately determine the indices of refraction as well as the biological stability of-the resultant IOL.

The collagen-based preparations readily adhere to tissue, such as a lens capsule, and exhibit sufficient surface tension to prevent the solution from flowing out the capsular sac. Moreover, the injectable collagen solutions are transparent, biologically stable, and appear to inhibit epithelial cell proliferation. No epithelial cell accumulation was noted after injection into the lens capsule in rabbit model studies.

Upon injection into the capsular sac, the collagen solution either remains in its original unpolymerized state or may undergo subsequent polymerization to form a gelatinous lens. Polymerization in the injection site may occur spontaneously or can be initiated by chemical or enzymatic means, or by photoinitiation.

Accordingly, it is an object of the invention to provide a method for preparing IOLs using injectable biologically compatible, modified collagen compositions. The modified collagen compositions are viscous, but injectable, transparent and have a predetermined refractive index. The range of the index of refraction is between about 1.2 and about 1.6. They are prepared by chemical modification of collagen derived from various animal sources with glutaric anhydride, other acylating agents, sulfonating agents or combinations thereof. The refractive index may be modulated by choosing the appropriate modification agent.

It is another object of the invention to provide collagen-based IOLs to replace diseased or natural lenses following their removal. The IOL should be clear, transparent, biologically stable and be able to inhibit or stabilize lens capsule epithelial cell accumulation. The IOL should exhibit refractive index similar to the natural lens (core-1.406 and cortex 1.386) or varied to correct various refractive errors following lens removal.

It is yet another object of the invention to provide collagen-based IOLs which can be used to replace an excised lens such that the IOL would not only correct any refractive errors of vision resulting from lens removal but would also allow the lens system to continue to accommodate. The collagen-based IOL can be used in patients to treat visual defects resulting from cataracts, presbyopia, myopia, hyperopia and trauma.

These and other objects of the invention will be apparent in light of the detailed description below.

DETAILED DESCRIPTION OF THE INVENTION

All patents, patent applications, and literature references are hereby incorporated by reference in their entirety.

As defined herein, the term "injectable collagen composition" refers to an injectable, chemically modified, biologically compatible collagen composition which, when injected into an evacuated lens capsular sac, forms a prosthetic lens. The injectable collagen composition fills the capsular sac and conforms to the dimensions of a natural crystalline lens which, in a human adult, measures approximately 4 mm in thickness and 9 mm in diameter. The term "biologically compatible" refers to collagen modified in accordance with the present invention which when incorporated or implanted into or placed adjacent to the biological tissue of a subject, does not deteriorate appreciably over time or induce an immune response or deleterious tissue reaction after such incorporation or implantation or placement.

The type of collagen useful in preparing the IOL of this invention is selected from the following groups: purified Type I collagen, Type IV collagen and Type III collagen, intact collagen-rich tissue or a combination of any of the foregoing. Preferred as a collagen starting material is purified Type I collagen derived from animal tissue or predominantly Type I collagenous product prepared from human tissue. Type I collagen is ubiquitous and readily extracted from animal tissues such as dermis and tendon. Common sources are bovine tendon and hide and rat tail tendon. Extraction from human tissues is difficult. U.S. Pat. No. 4,969,912, "Human Collagen Processing and Autoimplant Use", describes unique methods to disperse and solubilize human tissue.

A variety of collagen solubilization procedures that are well known in the art can be used to prepare the modified collagen solutions useful for the instant invention. Native collagen is liberated from non-collagen connective tissue constituents (lipids, sugars, proteins, etc.) and isolated after subjecting it to proteolytic enzymatic treatment by an enzyme other than collagenase. Suitable proteolytic enzymes include pronase and pepsin. The enzymatic treatment removes most of the immunogenic non-helical portions of native collagen (telopeptide) and provides a monomeric collagen material which is soluble in dilute acidic aqueous media. A solution containing the crude solubilized collagen is then subjected to a series of treatments to purify the soluble atelopeptide collagen by separating it from insoluble collagen, protease and noncollagen products resulting from the proteolytic enzymatic procedure. Conventional methods for preparing pure, acid soluble, monomeric collagen solutions by dispersing and solubilizing native collagen are described, for example, in U.S. Pat. Nos. 3,934,852; 3,121,049; 3,131,130; 3,314,861; 3,530,037; 3,949,073; 4,233,360 and 4,488,911. A method for preparing solubilized collagen solution is provided in the examples that follow.

The biological stability of the collagen based IOL of the invention appears to be affected by the solubility characteristics of the starting collagen as well as the extent of chemical modification. Completely solubilized modified collagen generally does not produce an IOL that is resistant to high concentrations of neutral proteolytic enzymes under laboratory testing conditions. Hence, in practicing this invention, it is preferred that prior to chemical modification, a solubilized collagen solution is converted to partially fibrillar collagen. Chemical modification of a partially fibrillar collagen solution results in a modified collagen composition which is clear, transparent and injectable. The use of partially fibrillized collagen as the preferred starting material for the modification process results in an IOL with improved resistance to degradation by neutral proteolytic enzymes, such as trypsin.

To prepare a partially fibrillized collagen solution, a solubilized collagen solution is adjusted to pH between about 7.0 and 7.6, preferably about 7.4, and allowed to undergo limited fibrillogenesis at a temperature between about 25° C. and 40° C., preferably about 37° C. , for a period of between about 10 and 30 minutes, preferably about 20 minutes.

Figure 3:
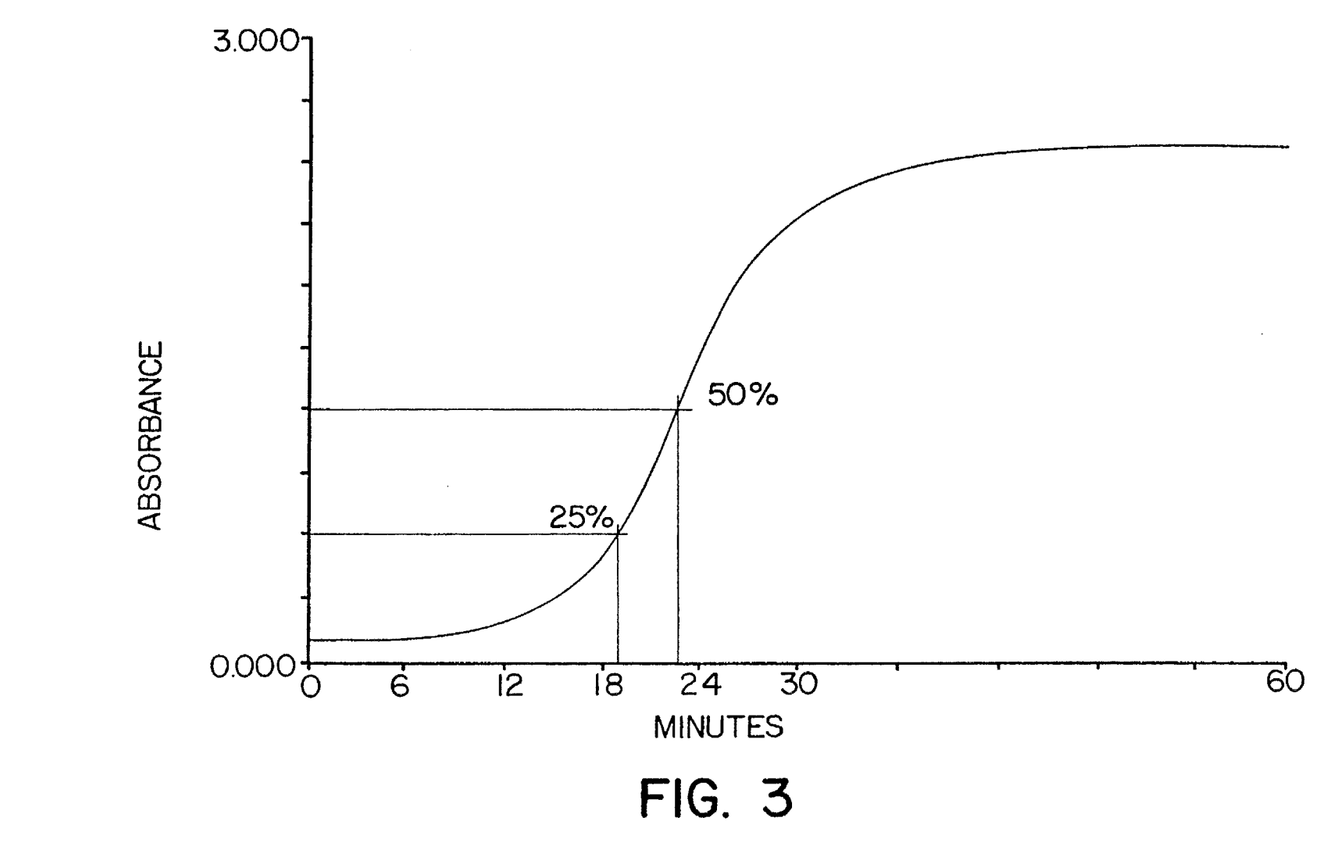
FIG. 3 illustrates an absorbance spectrum of a purified, acid soluble collagen solution (collagen concentration of 30 mg/ml) undergoing limited fibrillogenesis. At T=0 the solution pH was adjusted to 7.2 using 2.5N NaOH and mixed well at 25° C.

The extent of fibrillogenesis can be ascertained by measuring the increase in turbidity of the solubilized collagen solution by absorption spectroscopy (FIG. 3). In general, fibrillogenesis is permitted to continue until the turbidity of the solution becomes about 20% to 60% greater, preferably about 25% greater, than the absorbance of the initial solution.

Without being bound to any mechanism or theory of collagen fibrillogenesis in this invention, it is believed that a portion of the solubilized collagen molecules undergoes self-assembly to form microfibrils which can be observed microscopically. For a discussion of the fibrillogenesis process, see Nimni, M. E. "Collagen: Vol. I Biochemistry," CRC Press, Inc.; Boca Raton, Fla., USA (1988), pages 7–16 and Silver, F. H. in "Biological Materials: Structure, Mechanical Properties, and Modeling of Soft Tissues", New York University Press, New York; N.Y. (1987), pages 137–163.

After chemical modification, the partially fibrillar collagen composition loses its turbidity and turns clear and transparent. Collagen microfibrils in the chemically modified partially fibrillar collagen solutions can no longer be observed microscopically. The modified partially fibrillar collagen solution is believed to include modified collagen molecules and modified collagen aggregates containing collagen molecules.

In general, useful chemical modifier agents are those which react covalently with solubilized or partially fibrillar collagen to produce a modified collagen composition which is injectable, optically transparent, biologically stable and compatible, and which resists epithelialization and degradation by proteolytic enzymes.

Depending on the choice of modifier and the extent of modification, chemical modification of collagen imparts an appropriate index of refraction to the composition. Other desirable features which may be imparted to the modified collagen composition include UV blockage ability, and polymerizability.

Suitable acylating agents for use in the instant invention include aliphatic, alicyclic and aromatic anhydrides or acid halides. Non-limiting examples of acylating agents include glutaric anhydride, succinic anhydride, lauric anhydride, diglycolic anhydride, methylsuccinic anhydride, methyl glutaric anhydride, dimethyl glutaric anhydride, succinyl chloride, glutaryl chloride, lauryl chloride, phthalic anhydride, methacrylic anhydride, trifluoroacetic anhydride, styrene/maleic anhydride co-polymer, and ethylene/maleic anhydride copolymer. These chemicals are available from Aldrich Chemical Company (Milwaukee, Wis.). Preferred acylating agent for use in the present invention are glutaryl anhydride, methacrylic anhydride, trifluoroacetic anhydride, ethylene/maleic anhydride copolymer, and phthalic anhydride. An effective amount of an acylating agent is broadly between about 0.5 and 20% wt total collagen, preferably between about 3 and 10% total collagen in solution.

Useful sulfonating agents for the preparation of modified collagen monomers of the present invention include aliphatic, alicyclic and aromatic sulfonic acids or sulfonyl halides. Non-limiting examples of sulfonating agents for use in the present invention include anthraquinone-1, 5-disulfonic acid, 2-(chlorosulfonyl)-anthraquinone, 8-hydroxyquinoline sulfonic acid, 2-naphthalene- sulfonyl chloride, beta-styrene sulfonyl chloride, 2-acrylamido-2-methyl-1-propane sulfonic acid, aniline-2-sulfonic acid, fluorosulfonylbenzene sulfonyl chloride, and poly (vinyl) sulfonic acid. These chemicals are also available from Aldrich Chemical Company (Milwaukee, Wis.). Preferred sulfonating agents for preparing the adhesive collagen materials are beta-styrene sulfonyl chloride, and aniline-2-sulfonic acid. Such compounds, in non-toxic effective amounts, can be safely employed in collagen-based intraocular lens. An effective amount of sulfonating agent is broadly between about 0.5 and 20 wt % of the total collagen, preferably between about 1 and 10 wt % of the total collagen in solution.

Non-limiting combinations of acylating agents and/or sulfonating agents include glutaric anhydride/beta-styrene sulfonyl chloride/methacrylic anhydride; glutaric anhydride/ethylene/maleic anhydride copolymer/methacrylic anhydride; glutaric anhydride/polyvinyl sulfonic acid/methacrylic anhydride; and glutaric anhydride/ethylene/maleic anhydride copolymer/styrene/maleic anhydride copolymer. Preferred combinations for use in the present invention are glutaric anhydride/beta-styrene sulfonyl chloride; glutaric anhydride/phthalic anhydride; and glutaric anhydride/ aniline-2-sulfonic acid.

When combinations of two or more acylating agents, sulfonating agents, or mixtures of both agents are used for preparation of modified collagen composition, the total amount of chemical modifiers is preferably between about 3 and 10% wt of collagen in solution. Excess quantities of chemical modifiers beyond the preferred range may result in a collagen composition that is biologically unstable and sensitive to tissue proteases.

Modification of collagen is carried out at alkaline pH, in a range between about 7.5 and 10.0, preferably between about 8.5 and 9.5, and most preferably at about pH 9.0. The acylation reaction can be monitored by the decrease in pH. The reaction is terminated when the pH value remains stable at between about 5 and 8, preferably about 6.5 and 7.5. The reaction can also be monitored by removing aliquots and measuring the free amine concentration of the modified collagen solution as compared to the starting solution of collagen.

The modification reaction should be complete in between about 5 and 90 minutes, preferably between about 20 and 40 minutes. The reactions should be carried out at temperatures between about 0° C. and 37° C., preferably between about 4° C. and 25° C.

The reaction can be stopped by adjusting the pH to about 12.0 for about 2 minutes. This destroys residual, unreacted chemical modifiers. The modified collagen is then precipitated by reducing the pH using hydrochloric acid, acetic acid, nitric acid, sulfuric acid, or other acid.

The amount of acid must be sufficient to precipitate out the chemically modified collagen. Generally precipitation occurs at a pH between about 3.5 and 6.0, preferably between about 4.0 and 5.0.

The precipitate of reacted collagen which now contains substituent groups reacted with amine groups (primarily epsilon-amino groups), is recovered from the mixture using conventional techniques such as centrifugation or filtration. Centrifugation at between about 3,000 and 15,000 rpm for between about 20 and 60 minutes, preferably between about 4,000 and 12,000, for between about 20 and 30 minutes provides efficient recovery of the precipitate.

After recovery, the precipitate is washed with deionized water and subsequently dissolved in a physiological solution, e.g., phosphate buffer (0.1M) at about pH 7.2. It may be necessary to adjust the pH between about 7.0 and 7.5. This can be done, for example, by the addition of sodium hydroxide solution.

Following dissolution of the precipitate, the solution is generally filtered by conventional filtering means, i.e. a 5 micron filter, and then centrifuged to remove air bubbles. At this point, the resulting solution containing chemically modified collagen molecules and aggregates exhibits a viscous consistency, varying degrees of transparency and clarity, and a characteristic refractive index depending on the choice of chemical modifiers, the extent of acylation and on the state of solubility of the starting collagen material.

The viscosity of the injectable modified collagen solution, determined at a temperature of about 25° C., is broadly between about 30,000 centipoise and 300,000 centipoise, preferably between about 75,000 and 150,000 centipoise. Viscosity of the solution may be adjusted by the addition of buffer or collagen precipitate.

The indices of refraction of the modified collagen solution, determined at a temperature of about 25° C., are broadly in the range of between about 1.325 and 1.425, preferably between about 1.350 and 1.425. The refractive index of the collagen-based solution can be manipulated by modifying the soluble collagen with the appropriate aforementioned agents and by regulating the extent of chemical modification.

The extent of modification may be modulated by varying the amount of chemical modifiers, the pH, the temperature and the time of the reaction. In addition, the method of addition of the modifying agents will affect the reaction. Reactions are generally slower if the chemical agent is added as a solid or powder rather than as a solution.

The extent of modification also determines the biological stability of the collagen-based IOL. Complete modification results in a collagen lens that rapidly degrades in the presence of neutral proteolytic enzymes, such as trypsin. It has been discovered that the biological stability of collagen-based IOL can be manipulated by controlling the extent of chemical modification.

Figure 1:
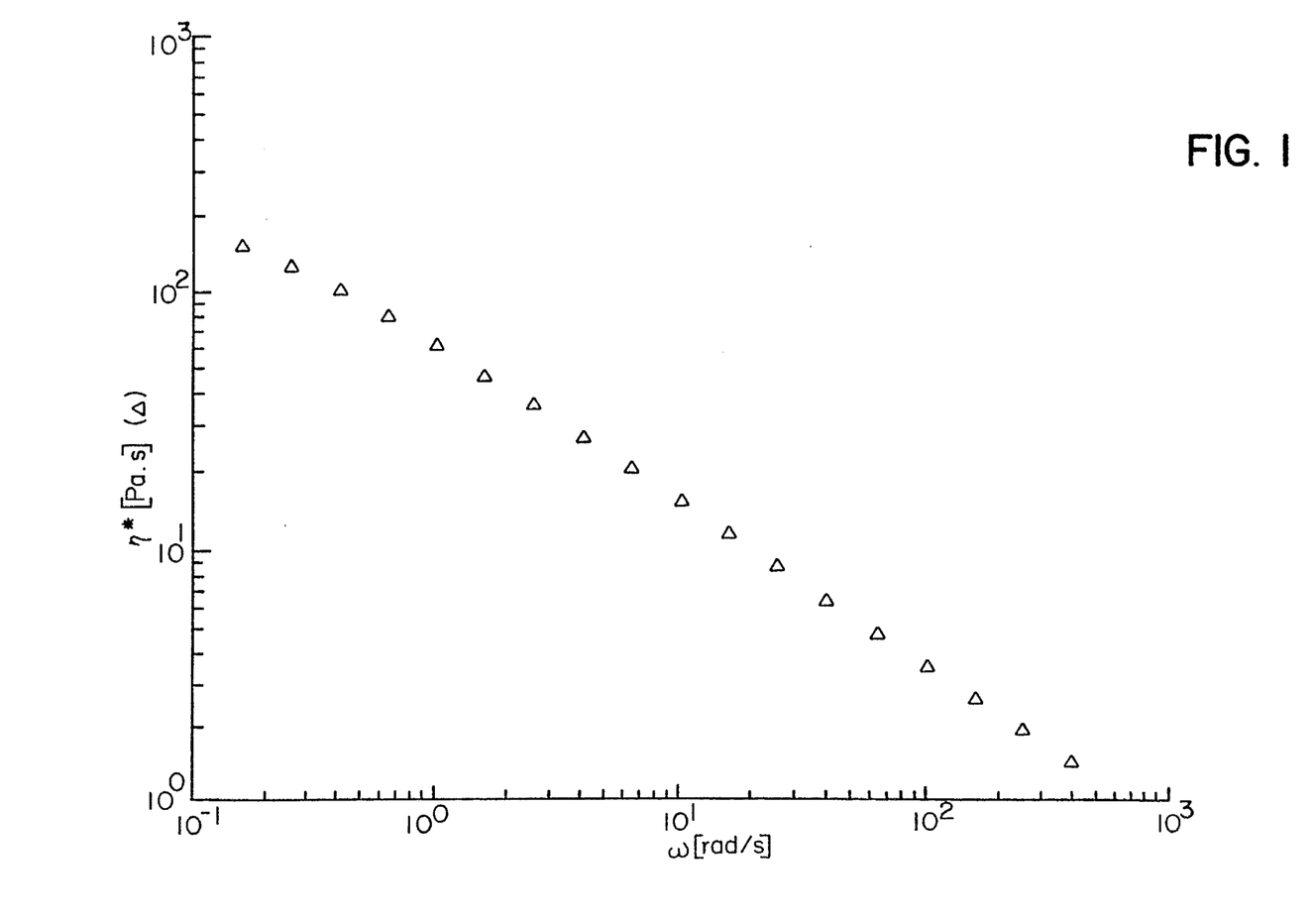
FIG. 1 illustrates that glutaric modified collagen solutions, prepared in accordance with Example 5, are psuedoplastic and thus exhibit shear thinning as shear rate increases. The rheometric analysis was performed on a Rheometrics System IV rheometer (Rheometrics Piscataway, N.J.) using a 50 mm cone and plate at 0.04 radians. The temperature employed was 30° C.

The modified collagen solutions are psuedoplastic as such solutions exhibit shear thinning as shear rate increases, typical of psuedoplastic solutions. FIG. 1 illustrates this property in glutaric modified collagen prepared in accordance with Example 5. They are also thixotropic as such solutions regain their original viscosity after thinning due to shear such as injection through a syringe.

Figure 2:
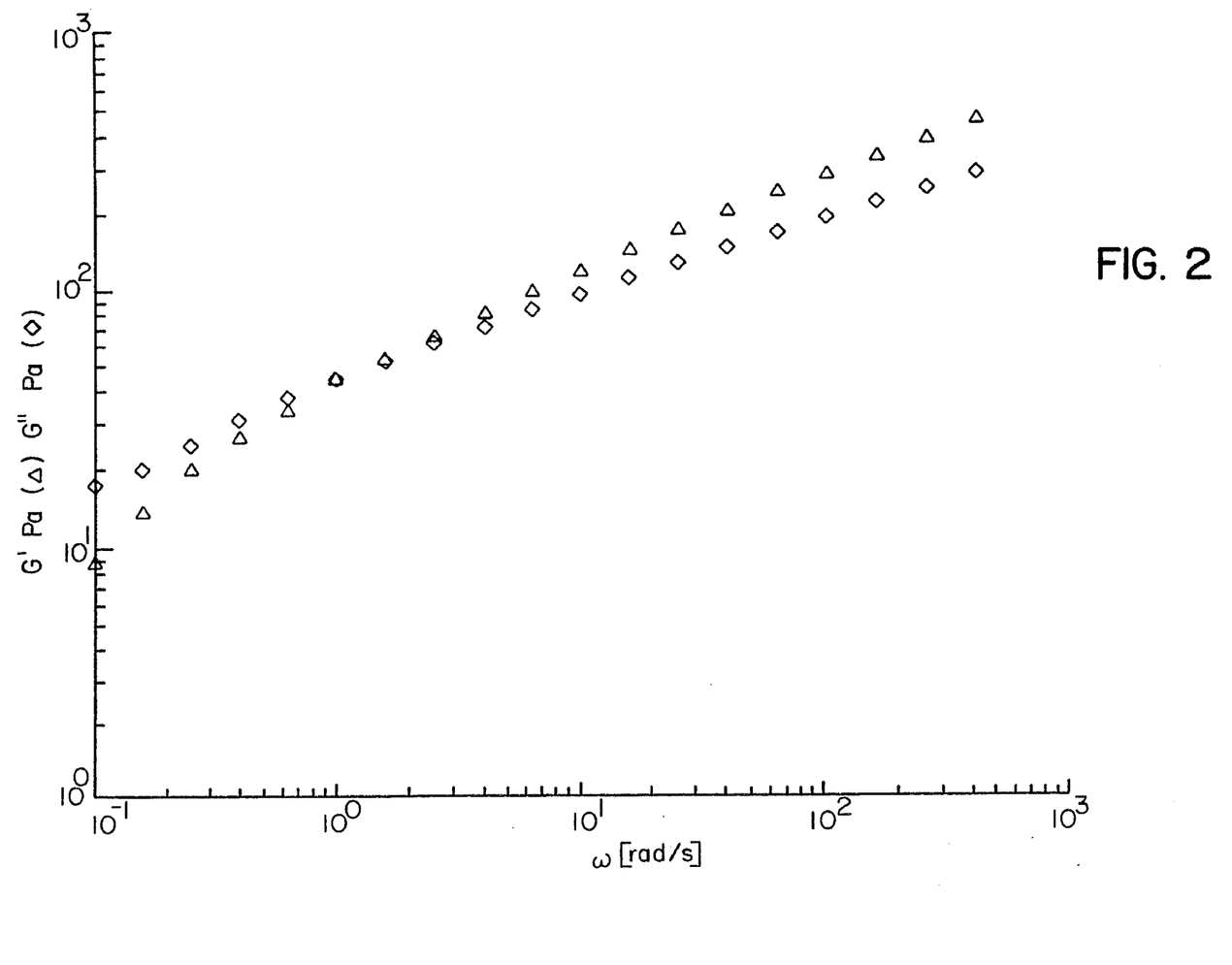
FIG. 2 illustrates that glutaric modified collagen solutions, prepared in accordance with Example 5, are viscoelastic. The G' component represents the elastic or storage modulus and the G" component represents the viscous or loss modulus. The conditions employed are the same as described in FIG. 1.

In addition, the modified collagen solutions are viscoelastic as shown in FIG. 2 for glutaric modified collagen solution also prepared in accordance with Example 5. FIG. 2 is typical of viscoelastic solutions and illustrate that viscoelasticity is an important characteristic for an injectable collagen solution. In this figure, G' represents the elastic modulus of the material and G" the viscous modulus of the material. As the shear rate increases, the elastic component becomes more important than the viscous component. Materials without elastic properties do not exhibit a G' component. For a review of the properties of viscoelastic collagen solutions, see U.S. Pat. Nos. 4,713,446 and 4,851,513.

The chemically modified collagen compositions are injected into the lens capsule to form the IOL. They should be injectable through a cannula with a inside diameter preferably no greater than about 1.0 mm, clear and colorless, essentially nonbiodegradable, and of a refractive index similar to that of natural lens material. The collagen compositions can be prepackaged in ready-to-use syringes containing materials exhibiting several different indices of refraction.

Upon injection of the collagen compositions to form the IOL, the material should not diffuse through the lens capsule into adjacent ocular tissues. The optimal lens substitute material will replace the lens, allowing accommodation, and also correct any refractive errors of vision resulting from removal of cataracts or from removal of the natural lens to treat presbyopia, myopia and hyperopia.

The collagen-based IOL can either remain in its unpolymerized state or can be further polymerized in situ within the sac. Several formulations of the injectable modified collagen compositions, e.g. methacrylic anhydride/glutaric anhydride collagen, may undergo spontaneous or induced polymerization in situ; however, it is not necessary for the collagen material to undergo polymerization to be an effective lens material.

The polymerization or crosslinking of the modified collagen composition can be carried out by simply exposing the material to atmospheric oxygen, although the rate of polymerization is appreciably slower in the absence of polymerization agents such as UV irradiation or chemical initiator agents.

Polymerization may be induced by a variety of means such as irradiation with UV or fluorescent light. When irradiation is employed, short wave UV irradiation is preferred. UV irradiation may be accomplished in the short wave length range using a standard 254 nm source or using UV laser sources. With a standard 254 nm source of between about 4 and 12 watts, polymerization generally occurs in between about 10 and 40 minutes, usually in between about 20 and 30 minutes, at an exposure distance of between about 2.5 and 10 cm, preferably between about 2.5 to 5 cm distance. Excess UV exposure will begin to depolymerize the collagen polymers.

Polymerization of the modified collagen solution in the presence of oxygen can also be achieved by adding an initiator to the solution prior to injection of the modified collagen composition into the sac. Non-limiting examples of initiators include sodium persulfate, sodium thiosulfate, ferrous chloride tetrahydrate, sodium bisulfite and oxidative enzymes such as peroxidase or catechol oxidase. When initiators are employed, polymerization occurs in between about 30 seconds and 5 minutes, usually in between about 1 and 3 minutes.

A skilled artisan will appreciate that the indices of refraction of the polymerized collagen may be different from the initial unpolymerized modified collagen composition and will need to make an appropriate choice of modifier and extent of modification to achieve the index of refraction desired in the polymerized collagen composition. For example, the desired index of refraction of the polymerized collagen would be dependent on the index of refraction of the unpolymerized modified collagen composition which, in turn, is influenced by a number of factors such as choice of chemical modifier and extent of modification.

A variety of additives may be incorporated into collagen compositions to enhance the stability of the resultant IOL. Suitable, but not limiting, examples include antioxidants and photodegradation retardants. Such additives may incorporated by simple addition or by chemical linkage to collagen compositions before or after modification but prior to injection.

For example, suitable antioxidants for use in this invention include glutathione/glutathione reductase, ascorbic acid, quinone derivatives such as PQQ (pyrroloquinoline quinone), EEDQ (2-ethoxyl-1-ethoxycarbonyl-1,2-dihydroquinoline), and 8-hydroxyquinoline-5-sulfonic acid. Likewise, UV blockers such as benzophenone derivatives (e.g. 3,3', 4,4'-benzophenone tetracarboxylic dianhydride) and benzotriazoles can be incorporated into the injectable collagen compositions.

The examples set forth below are intended to illustrate the invention without limiting its scope.

EXAMPLE 1

Preparation of Acid Soluble Type I Collagen Solution

Fibrous Type I collagen was prepared from bovine material (calf hide) using the following procedure:

Clean, dehaired split hides were purchased from the Andre Manufacturing Co. (Newark, N.J.) and frozen until ready for use. Approximately 200 g of calf hide were thawed at room temperature and cut into approximately 1 cm$^3$ pieces using a scalpel and tweezers. The weight of the wet tissue was recorded. The calf hide was then placed into 15 liters of 0.5M acetic acid and stirred with a lightening mixer at room temperature for at least one hour. A 10 mL solution of 0.5M acetic acid containing 2% w/w (or 3.9 g) pepsin from porcine mucosa (Sigma Chemicals, St. Louis, Mo.) was added to the calf hide solution. This solution was stirred overnight with a lightening mixer at room temperature. An additional 10 mL 0.5M acetic acid solution containing 1% w/w (or 1.96 g) pepsin was added to the calf hide mixture. The solution was again stirred overnight with a lightening mixer at room temperature. The dissolved calf hide solution was refrigerated overnight until a uniform temperature of 4° C. was reached. The pH of the solution was adjusted to 9.0 with 10N NaOH to denature pepsin. Stirring was maintained throughout the pH adjustment process with a lightening mixer. As collagen will precipitate out at pH 9.0 when the temperature is above 6° C., ice cubes were added directly to maintain the 4° C. temperature. The solution is then refrigerated for at least four hours, then centrifuged at 4° C. for 30 minutes at 9 rpm. The resulting pellet, containing pepsin, was discarded. The supernatant, containing collagen, was subjected to a series of purification steps.

The collagen solution was subjected to a diafiltration process to remove residual pepsin and low molecular weight components. An Amicon Model DC10L/DC10LA ultrafiltration system with a spiral membrane cartridge (SY0100) with a 100,000 kD molecular weight cut off was used.

Thereafter, collagen was precipitated out by addition of solid NaCl to the supernatant to a final concentration of 2.5M. The solution was stirred at room temperature for at least two hours. The collagen precipitate was collected by centrifugation of solution for 30 minutes at 9000 rpm and redissolved in 15 liters of 0.5M acetic acid, a process requiring at least 2 hours. Collagen was reprecipitated out again by addition of solid NaCl to the solution to a final concentration of 0.8M. The solution was stirred for at least two hours and the collagen collected by centrifugation of the solution for 30 minutes at 9000 rpm. This redissolving/precipitation procedure was repeated once more. The final pellet, containing purified collagen, was dissolved in 0.1M acetic acid of sufficient volume to provide approximately 0.3% w/w collagen Type I solution of pH 3.0. The collagen solution was then filtered through a 0.45 micron filter to remove particulate matter and sterilized through a 0.22 micron filter. The solubilized collagen solution, containing a collagen concentration of about 30 mg/ml, can now be used in the modification process.

EXAMPLE 2

Clear, transparent lenses formed by methacrylic anhydride/glutaric anhydride modified collagen 100 mL of a solution containing soluble, bovine, atelopeptide collagen at a concentration of approximately 25 mg/ml was reacted at pH 9.0 with two drops of methacrylic anhydride and 24 mg of glutaric anhydride in 0.5 mL of dimethylformamide. After 20 minutes, the pH was reduced to 4.3 and the pellet recovered and washed 2 times. The resulting precipitate was dissolved in 0.005M phosphate buffer and the pH adjusted to 7.0. To this was added 1.0 mL of sodium persulfate solution (15 mg in 1 mL of buffer). Aliquots of this clear, viscous solution having a viscosity of 75,000 cps were placed in quartz concave molds (diameter 7 mm, 5.5 mm base curve) and exposed to UV irradiation for 3 minutes. The solution rapidly polymerized to form thick, clear, transparent lenses having a refractive index of 1.390.

EXAMPLE 3

Phthalic anhydride modified collagen

Pure, atelopeptide, collagen was extracted from bovine hide and purified using differential salt precipitation as described in Example 1. A collagen solution containing about 30 mg/ml of collagen in 0.5M acetic acid was filtered through a sterile 0.22 micron filter. A 250 ml aliquot of the collagen solution was brought to pH 7.2 and placed in a 37°

C. water bath to initiate fibrillogenesis. When fibril formation was visible (the solution turns cloudy), the pH was increased to 9.0. Approximately 10 mg of phthalic anhydride in dimethyl formamide were added while the solution was mixed using a stir bar. The pH was maintained between 8.0 and 9.0 by adding 1N NaOH dropwise. After 30 minutes the pH was decreased to 7.2 and the mixture allowed to equilibrate to 37° C. to precipitate any unmodified collagen. The mixture was centrifuged at 3500 RPM for 20 minutes and the clear supernatant adjusted to pH 4.3 to precipitate the phthalic modified collagen. The precipitate was recovered by centrifugation at 3500 RPM and washed with water for injection three times. The final precipitate was dissolved in 0.005M phosphate buffered glycerol and the pH adjusted to about 7.2. The viscosity of the solution was greater than 100,000 cps and was diluted with additional buffer to a final concentration of 1.6% collagen. The viscous material was clear, slightly yellow and transparent. Aliquots were removed for protein concentration measurement based on the hydroxyproline method (Woessner, J. F. in "The Methodology of Connective Tissue Research," D. A. Hall, ed.; Joynson-Bruvvers Ltd, Oxford; 1976, pages 227–233).

EXAMPLE 4

2-Chlorosulfonyl anthraquinone modified collagen

Purified collagen solution was prepared as previously described in Example 1. Following filtration through a 0.2 micron filter, 250 ml of the collagen solution having a collagen concentration of about 30 mg/ml was brought pH 9.0 and reacted with 30 mg of 2-(chlorosulfonyl)-anthraquinone for a period of 30 minutes. Glutaric anhydride (10 mg) was then added and the reaction was again allowed to proceed for an additional 30 minutes. The pH was then adjusted to 7.4 and the material warmed to 37° C. to precipitate collagen molecules not modified sufficiently to prevent fibril formation. The neutral pH mixture was centrifuged to remove precipitates and the supernatant adjusted to pH 4.3 to precipitate modified collagen. The precipitate was recovered by centrifugation at 3500 rpm for 20 minutes and then washed three times with sterile water. The final precipitate was dissolved in phosphate buffered glycerol, 0.005M with 2% glycerol at pH 8.1, and pH adjusted to pH 7.4. The final solution was very viscous, slightly yellow, and transparent. Syringes were filled with the solution after the latter were filtered through a 5 micron filter. The solutions in the syringes were deaerated by centrifugation. The viscosity of the anthraquinone collagen formulation was too high to measure, i.e., greater than 100,000 cps. The refractive index of this composition was 1.3386.

The anthraquinone formulation appears to undergo spontaneous polymerization, probably resulting from oxidative processes. This was observed by examining the physical properties of the viscous material with time and noting that the material polymerized into a soft gel.

EXAMPLE 5

Evaluation of a Collagen-based IOL in Rabbits
A. Evaluation of glutaric modified Collagen Material A glutaric anhydride collagen formulation, containing approximately 1.5% (w/w) glutaric anhydride in total collagen, was prepared and evaluated in a rabbit. Collagen modification was accomplished by reacting 100 ml of pure, soluble collagen at 2.8 mg/ml with 8 mg of glutaric anhydride. Before modification, the collagen solution was adjusted to pH 7.2 and incubated at 37° C. for 15 minutes to allow for limited fibrillogenesis. The modified collagen was precipitated by adjusting the pH of the reaction mixture to about 4.5 and the precipitate was recovered by centrifugation at 3200 rpm and washed three times with sterile water. The final pellet was dispersed in 0.005M phosphate buffer containing 2% sterile glycerol (pH 7.6). The collagen dispersion was then filtered through a 5 micron filter and centrifuged to remove air bubbles. The deaerated solution was transferred to a 2.5 ml glass syringe and placed in a sterilization pouch. The refractive index of this collagen was 1.363.

Aliquots of the clear, viscous solution were placed over the surface of a rabbit cornea from which the epithelium was removed. The material was then subjected to short wave length UV irradiation in nitrogen to polymerize the collagen. A thin, amorphous, clear film resulted. The eye was examined for several days to evaluate reepithelialization of the surface. Epithelial cells appeared to migrate to the collagen film and then stop, suggesting that this particular formulation may inhibit epithelial cell migration and cell growth. This is a desirable characteristic for a material to fill the lens capsule. Other materials that have been evaluated to replace the natural lens by implantation in the lens capsule (i.e. silicones) have failed due to excessive accumulation of epithelial cells lining the lens capsule. This interface of cells results in opacification of the lens.

B. Placement of a Collagen-based IOL in a Rabbit Model

The ophthalmologic surgery was performed with a rabbit model. The natural lens was removed by phacoemulsification leaving the lens capsule intact except for the flap needed to insert the phaco tip. Removal was difficult and resulted in a flap larger than desired. After aspiration of the lens fragments, about 1.0 and 1.5 mL of the collagen solution was injected into the lens capsule, reforming the lens to about its normal volume.

The animal was observed by slit lamp examination for the next 15 weeks. There was no indication of tissue reaction nor of inflammation and the injected lens remained clear and transparent. After 15 weeks, the eye was enucleated and prepared for histopathology. Examination immediately following enucleation showed that the collagen had polymerized into a soft, pliable, gelatinous material which was optically clear, and about the size and shape of the natural rabbit lens. There was no discoloration or presence of particulates. Pathological examination indicated a clear, transparent amorphous lens composition. This preliminary evaluation was extremely encouraging, especially since the flap in the anterior capsule was large and no attempt was made to seal the injection site.

EXAMPLE 6

Resistance to Neutral Protease and Collagenase

In this example, pure, soluble collagen was prepared as previously described in Example 1. Following filtration through a 0.2 micron filter, the solution was brought to pH 7.0 and placed in a water bath at 37° C. to initiate collagen fibrillogenesis. After approximately 15 minutes, the solution became cloudy. At this point 100 ml of solution at 2.8 mg/ml collagen was adjusted to pH 9.0 and 7.0 mg of glutaric anhydride was added. The reaction was allowed to continue for another 20 minutes. The pH was then decreased to 4.3 to precipitate the modified collagen. The precipitate was recovered by centrifugation and was washed three times. The final precipitate was very fine and granular. This was dissolved in phosphate buffer and adjusted to pH 7.0–7.4. The viscous solution was clear to slightly cloudy. Films were prepared and exposed to UV irradiation for 20 minutes. Samples were then evaluated for resistance to neutral protease (trypsin) and to vertebrate collagenase. These results were compared to standard glutaric collagen (excess glutaric anhydride). Table 1 shows the results from such evaluation.

TABLE 1

RESISTANCE TO NEUTRAL PROTEASE AND COLLAGENASE RESISTANCE (%), 24–25 HOURS

|  | Buffer | Trypsin | Vertebrate Collagenase |
|---|---|---|---|
| Standard Glutaric | 95 | 30 | 30 |
| Resistant Glutaric | 100 | 87.4 | 94.7 |

EXAMPLE 7

Glutaric Collagen Prepared From Rabbit Skin

Approximately 10 g of rabbit skin, obtained from New Zealand White Rabbits, was dissected to recover the dermal layer. Approximately 2.2 g of wet dermis were obtained. The dermis was immersed in 95% specially denatured ethyl alcohol (SDA-4, J. T. Baker, Inc., Phillipsburg, N.J.) for 16 hours and then placed in 20 ml of 0.04M Tris buffer (pH 8.5) containing 0.85% NaCl After 4 hours, the rabbit dermis was minced with scissors and pulverized by three 30 second pulses with a OMNI homogenizer (Omni International, Waterbury, Conn.) with a 10 mm generator. Three separate aliquots of solid glutaric anhydride at 5% (w/w) of the wet dermic weight was then added to the pulverized dermis aliquots. After each addition, the tissue was again pulverized for three-30 second pulses. The rabbit tissue appeared to disperse into a cloudy gelatinous mass with no fiber units. The dispersed rabbit dermis was then diluted to 50 ml with 0.04M Tris buffer (pH 8.5) and pH of the solution was reduced to about 4.3. A large fibrous mass formed which was then washed three times with sterile water and dissolved in 3 ml of phosphate buffered saline (5 mM phosphate buffer with 0.85% NaCl at pH 7.4). A viscous, clear solution formed which was then placed in three 1.0 ml syringes for use as an injectable IOL in rabbit models.

EXAMPLE 8

Glutaric Collagen Prepared From Human Skin

Approximately 2.8 g of human skin was obtained from 3.5 mm biopsy punches. The biopsies were stored in 95% specially denatured ethyl alcohol (SDA-4) and then dissected to recover the dermal layer. Dermal sections, 0.8 g, were placed in 0.85% NaCl overnight and then transferred to 0.05M Tris buffer, pH 8.5, for 2 hours. The sections were minced with scissors and pulverized with an OMNI homogenizer having a 10 mm generator. Three 30 second pulses were employed in the pulverization process. Two separate 12.5 mg aliquots of solid glutaric anhydride was added to the pulverized tissue. After each addition, the tissue was again pulverized for three 30 second pulses.

The tissue appeared to disperse well into a mixture of gelatinous material and fibers. The mixture was centrifuged at 3200 rpm for 20 minutes and the fibrous pellet discarded. The cloudy supernatant was adjusted to pH 4.3 to precipitate the modified dermal collagen. The precipitate was washed three times with sterile water and then dissolved in phosphate buffered glycerol (2% glycerol in 4 mM phosphate buffer, pH 7.4) to form a relatively clear, viscous material. This material was filtered through a 5 micron syringe filter and the resulting clear solution centrifuged at 8,000 rpm to remove air bubbles. The final solution was transparent and had a viscosity of 85,000 cps. The material was placed in quartz concave molds (diameter 7 mm, 5.5 mm base curve) and exposed to 254 nm UV irradiation for 15 minutes. The resultant molded lens exhibited a refractive index of 1.424. The lens was placed in a 0.02% trypsin solution (50 mM TRIS buffer, 150 mM NaCl 1 mM $CaCl_2$, 1 uM $ZnCl_2$ and 0.05% $NAN_3$, pH 8.0) and incubated at 37° C. After two weeks, no observable degradation of the lens was observed.

What is claimed is:

1. A method of making an intraocular lens in an intact lens capsular sac comprising the steps of:

removing the natural lens from the capsular sac injecting a modified collagen composition into said lens capsular sac in an amount sufficient to fill said lens capsular sac; and exposing said modified collagen composition in said lens capsular sac to a polymerization agent so as to polymerize and form said intraocular lens.

2. The method according to claim 1 wherein said modified collagen composition has an index of refraction ranging between about 1.325 and about 1.425.

3. The method of forming an intraocular lens in a lens capsular sac, said natural lens having been removed from said lens capsular sac, comprising injecting a modified collagen composition into said lens capsular sac in an amount sufficient to form said intraocular lens and polymerizing said modified collagen composition in said lens capsular sac so as to form said intraocular lens.

4. The method according to claim 3, wherein said lens has an index of refraction ranging between about 1.325 and about 1.425.

5. The method according to claim 3, wherein said modified collagen composition comprises collagen modified with an acylating agent, a sulfonating agent, or combination thereof by an amount ranging between about 0.5 and about 20 wt. %, based on total collagen.

6. The method according to claim 3, wherein said modified collagen composition comprises partially fibrillar collagen or solubilized collagen.

7. The method according to claim 3, wherein said collagen comprises purified Type I collagen, purified Type III collagen, purified Type IV collagen, collagen rich tissue or a combination of the foregoing.

8. The method according to claim 3 wherein said collagen comprises Type I collagen.

9. The method according to claim 8 wherein said Type I collagen is derived from human tissue or animal tissue.

10. The method according to claim 9 wherein said Type I collagen comprises autogenic human tissue.

11. The method according to claim 5 wherein said acylating agent is selected from the group consisting of glutaric anhydride, succinic anhydride, lauric anhydride, diglycolic anhydride, methyl succinic anhydride, methyl glutaric anhydride, dimethyl glutaric anhydride, methacrylic anhydride, trifluoroacetic anhydride, ethylene/maleic anhydride copolymer, styrene/maleic anhydride copolymer, phthalic anhydride, and any combination of the foregoing.

12. The method according to claim 11 wherein said acylating agent comprises glutaric anhydride.

13. The method according to claim 5 wherein said sulfonating agent is selected from the group consisting of anthraquinone-1,5-disulfonic acid, 2-(chlorosulfonyl)-anthraquinone, 8-hydroxyquinoline sulfonic acid, 2-naphthalene sulfonyl chloride, beta-styrene sulfonyl chloride, 2-acrylamido-2-methyl-1-propane sulfonic acid, aniline-2-sulfonic acid, fluorosulfonylbenzene sulfonyl chloride, and poly(vinyl) sulfonic acid.

14. The method according to claim 13 wherein said sulfonating agent is beta-styrene sulfonyl chloride or aniline-2-sulfonic acid.

15. The method according to claim 3, wherein the modified collagen composition is polymerized by exposing said composition to air, light, an initiator, or an oxidative enzyme.

16. The method according to claim 15, wherein said initiator is selected from the group consisting of sodium persulfate, sodium thiosulfate, ferrous chloride tetrahydrate, sodium bisulfite and a combination of the foregoing.

17. The method according to claim 15, wherein said oxidative enzyme comprises peroxidase and catechol oxidase.

* * * * *